United States Patent [19]

Pansiera

[11] Patent Number: 5,776,086
[45] Date of Patent: Jul. 7, 1998

[54] HINGE SYSTEM FOR AN ORTHOPEDIC BRACE

[76] Inventor: Timothy T. Pansiera, 735 N. Fork Rd., Barnardsville, N.C. 28709

[21] Appl. No.: 584,775

[22] Filed: Jan. 11, 1996

[51] Int. Cl.$^6$ ................................................ A61F 5/00
[52] U.S. Cl. ................................. 602/16; 602/26
[58] Field of Search ..................... 602/5, 16, 23, 602/26

[56] References Cited

U.S. PATENT DOCUMENTS

| | | | |
|---|---|---|---|
| 1,257,297 | 2/1918 | Brown | 602/16 |
| 2,344,631 | 3/1944 | Paley et al. | 602/5 |
| 2,559,473 | 7/1951 | Slodek, Sr. | 602/16 |
| 2,943,622 | 7/1960 | Nelson | 602/16 |
| 3,826,251 | 7/1974 | Ross | 602/23 X |
| 4,456,003 | 6/1984 | Allard et al. | 602/23 X |
| 4,502,472 | 3/1985 | Pansiera | 602/16 |
| 5,419,754 | 5/1995 | Hutchins | 602/26 X |

FOREIGN PATENT DOCUMENTS

| | | | |
|---|---|---|---|
| 633007 | 1/1995 | European Pat. Off. | 602/16 |

*Primary Examiner*—Richard J. Apley
*Assistant Examiner*—Denise Pothier
*Attorney, Agent, or Firm*—M. K. Silverman

[57] ABSTRACT

A hinge system for an orthopedic brace includes a distal section including a substantially circular pivot area including a ratchet having several angular saw-tooth teeth, each defined by alternating major and minor arms, intersections of the arms defining alternating outer and inner vertices, each of the inner vertices tilted in a counter-clockwise direction, the inner vertices each defining total included angles of between about 75 and about 95 degrees, in which a ratio of the length of each major to minor arm is in a range of about 2:1 to about 3.5:1, the inner vertices also defining a virtual inner radius (of the ratchet) between each inner vertex and an axis of rotation of the pivot area, and each of the outer vertices defining a virtual outer radius between the vertices and the axis of rotation, in which each major arm of each tooth intersects a tangent of a circle defined by the outer radius at an angle in a range of about 20 to about 40 degrees and in which each minor arm of each tooth intersects the outer circle at an angle in a range of about 60 degrees to about 80 degrees. Further included in the system is a control section having a rotatable pawl having at least three saw tooth teeth complemental in geometry to the teeth of the ratchet of the pivot area, the pawl teeth selectably interdigitatable with the teeth of the teeth of the ratchet. The system also includes a biasing element for effecting selectable engagement of the teeth of the pawl with the teeth of the ratchet, and a release mechanism for pivotally disengaging the respective teeth to permit free rotational movement of the distal section relative to the control section of the orthopedic brace when a change in relative position of the distal and control sections is desired.

12 Claims, 6 Drawing Sheets

HINGE SYSTEM FOR AN ORTHOPEDIC BRACE

BACKGROUND OF THE INVENTION

The present invention relates to medical devices and, more particularly, to a hinge system for an orthopedic brace for assisting in movement of body limbs which are in an infirm or partially infirm state.

Devices of the type to which the invention relate are referred to as "orthotic." This name derives from the fact that such devices operate to support or assist injured or inoperative body limbs, as opposed to replacement a missing limb. Accordingly, the term orthotic, as used herein, is to be distinguished from the term prothesis which is generally defined as an artificial device to replace a missing body part or limb.

Any artificial joint, whether resilient in character or step-advance rotational in character, must exhibit sufficient potency to offer effective functioning of the affected limb, while avoiding excesses or insufficiencies of motion that might prove discomforting or injurious to the user. Accordingly, a certain limited degree of adjustability, versatility and the like in the motion of the functioning of such devices, is desirable.

Although the basic function of an orthotic device is to support a limb, it is therefore desirable to attain, to the degree feasible, limited motion and flexibility in specific directions and planes. Thus, an objective in all orthotic devices is the provision of fundamental support while, as an advantageous addition, providing versatility of motion that will, to the extent practical, resemble normal body motion. As an addition to enabling adequate support, versatility of motion, and adjustability to various positions, an orthotic device should be as simple as possible in its arrangement of parts so that ease of manufacture is attained and the functioning of the device is unobtrusive as possible from a cosmetic point of view.

The present invention is directed to an orthotic device which employs a pawl and ratchet which includes a resilient spring action to permit discreet and limited rotational movement of portions of infirmed limbs relative to each other in a manner intended generally to simulate normal motion of such limbs. Such orthotic devices will, typically, include a pair of relatively moveable support members attached respectively to different parts of the limb of interest, for example, the upper leg and lower leg. In addition, some form of articulation means for providing a resilient, or other controllable interconnection, between proximal and distal parts of such a support device, is inherent to the operation of such devices.

The prior art, as is known to the inventor, is reflected in his U.S. Pat. No. 4,502,472 which teaches a hinge means for an orthopedic brace which, in essence, the instant invention is an improvement of. The invention has improved upon the old design in its use of a four-sided receiver to receive the arms of the brace, whereas the old design only uses a three-sided receiver. The instant invention also provides an improved interlocking tooth design, with a lower profile tooth which allows easier passage of the locking mechanism over the teeth, and yet allows a more reliable mesh of the teeth, this preventing release thereof until the locking mechanism is disengaged. The prior art teaches only the use of gear teeth as a locking mechanism, without teaching preferred angular dimensions of the teeth to maximize the reliability of the interlock and step-advance functions.

Further, the instant invention utilizes stamped metal parts for construction of the hinge means, whereas the previous design does not teach the advantages of the use of such stamped parts.

Other hinge means for orthopedic braces exist in the art, such as are reflected un U.S. Pat. No. 3,732,861 to Lehneis, and No. 4,090,264 to Thompson, but there are considered inappropriate to the present invention. None of these, or other references known to the inventor, address the problem solved herein; that is, the need for a rugged, efficient, sturdy, reliable and economical hinge for an orthopedic brace.

SUMMARY OF THE INVENTION

The instant invention is a hinge system for an orthopedic brace. The system comprises a distal section including a substantially circular pivot area including a ratchet depending therefrom, said ratchet having a plurality of angular saw-tooth teeth, each of said teeth defined by alternating major and minor arms thereof, intersections of said arms defining alternating outer and inner vertices, each of said inner vertices tilted in a counter-clockwise direction, said inner vertices each defining total included angles of between about 75 and about 95 degrees, in which a ratio of the length of each major to minor arm is in a range of about 2:1 to about 3.5:1, said inner vertices also defining a virtual inner radius, of said ratchet between said inner vertices and an axis of rotation of said pivot area, and each of said outer vertices defining a virtual outer radius between said vertices and said axis of rotation, in which each major arm of each tooth intersects a tangent of a circle defined by said outer radius at an angle in a range of about 15 to about 40 degrees and in which each minor arm of each tooth intersects said outer circle at an angle in a range of about 60 degrees to about 80 degrees. Further included in the system is a control section having a rotatable pawl having at least three saw tooth teeth complemental in geometry to said teeth of said ratchet area of said distal section pivot area, said teeth of said pawl selectably interdigitatable with said teeth of said distal section. The system also includes biasing means for effecting selectable engagement of said teeth of said pawl with said teeth of said ratchet, and release means for pivotally disengaging said respective teeth to permit free rotational movement of said distal section relative to said control section of the orthopedic brace when a change in relative position of the distal and control sections is desired.

It is a an object of the invention to provide a hinge system for an orthopedic brace to enable it to accomplish its fundamental support functions while, additionally, providing certain controlled motion in both the extension and flex direction.

It is another object to provide a hinge system for an orthopedic brace with angular teeth which provide additional strength for support and prevention of injurious slippage of the hinge.

It is a further object of the invention to provide a hinge system for an orthopedic device of a type having elements which are essentially integral with conventional parts of the orthopedic brace.

It is a yet further object to provide an effective, durable and economic hinge system for an orthopedic brace, where the hinge means are manufactured from machine-stamped metallic parts.

It is another object of the invention to provide an orthotic device that will function unobtrusively and yet be cosmetically advantageous to the user.

The above and yet further objects and advantages of the present invention will become apparent from the hereinafter set forth Brief Description of the Drawings, Detailed Description of the Invention, and Claims appended herewith.

DETAILED DESCRIPTION OF THE INVENTION

Figure 1A:
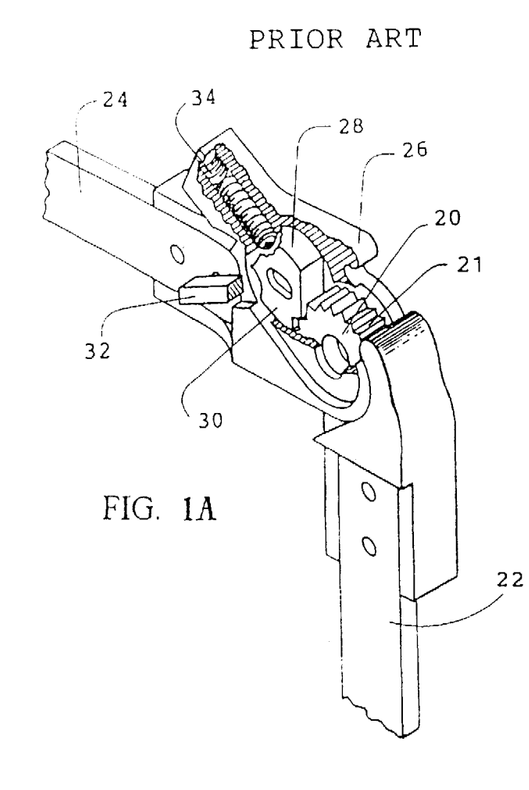
FIGS. 1A and 1B are views of a prior art orthotic hinge reflected in U.S. Pat. No. 4,502,472.
Figure 1B:
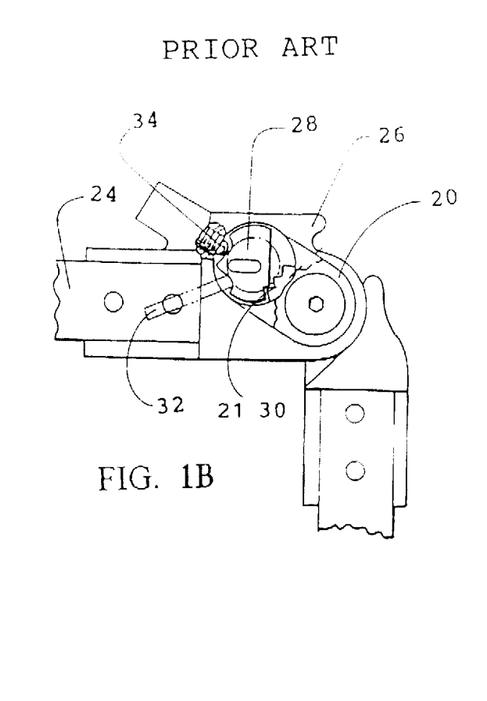

With reference to FIGS. 1A and 1B, there is shown in perspective and side breakaway views the mechanism of the orthopedic hinge of U.S. Pat. No. 4,502,472, of which the present invention is an improvement. More particularly, in the prior art of FIG. 1A and 1B there is shown an internal ratchet 20 which includes, at the circumference thereof, a multiplicity of teeth 21 each substantially constituting an equilateral triangle, that is, teeth in which each side thereof is defined by arm substantially equal in length to an opposite arm. In other words, the teeth reflected in the prior art FIGS. 1A and 1B possess both radial and axial symmetric.

As may be further noted, said ratchet 20 is integrally dependent from a distal rod 22 of the orthopedic brace. Further shown in the prior art of FIG. 1 is proximal section 24 of the brace which includes an integrally formed control section 26. Therewithin a pawl 28 which includes a plurality of teeth 30 which are complemental in geometry to said teeth 21 of the ratchet 20 is Changes in position of pawl 28 relative to ratchet 20 are effected by selective depressing of control lever 32. The degree of pressure between the teeth of the pawl and of the ratchet is controlled by pressure screw 34. It may, thereby, be appreciated that the integrity of the interlock between the ratchet and pawl of the prior art hinge is dependent upon the number of teeth which effect the interface, the angle at which the teeth create the interface, and the degree of pressure with which the pawl teeth are held against the ratchet teeth. Also, the ability to change positions of the pawl elements and, thereby, to permit the distal section of the brace to change its position relative to the proximal section thereof, is a function of the efficiency of the lever means 32 which is used to move the pawl relative to the ratchet.

Figures 2, 3:
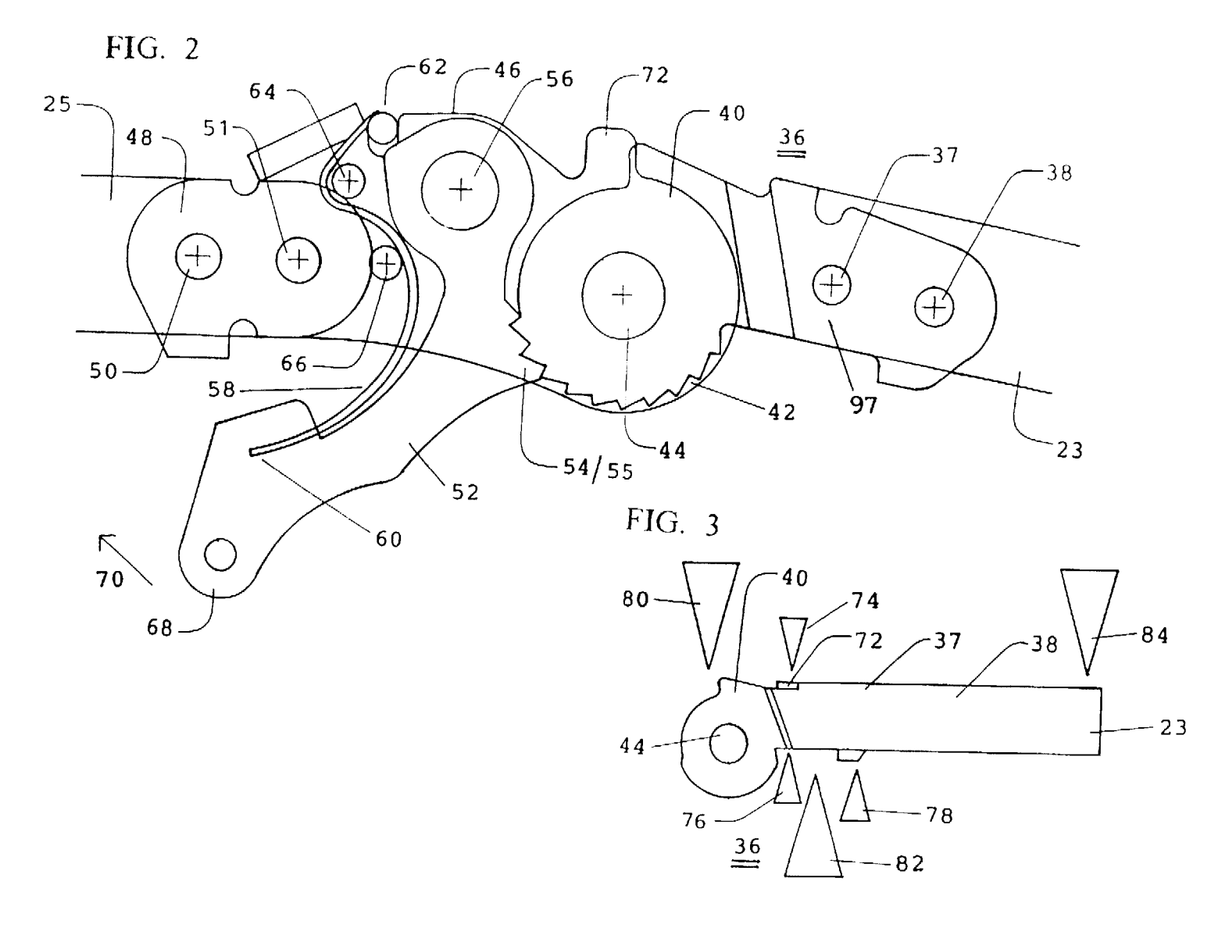
FIG. 2 is a side plan view shown the functional interaction between the major parts of the instant hinge system.
FIG. 3 is a side plan view of the ratchet portion of the invention.

The instant invention addresses the above noted weaknesses and limitations in the prior art through the use of a hinge system as is generally shown in FIG. 2. More particularly, there may, with reference to FIG. 2 be seen distal member 23 of an orthopedic brace and proximal member 25 thereof. Integrally secured to distal member 23 is a distal section 36 which is secured to the distal member 23 at rigid securement points 37 and 38 within a four sided distal receiver portion, more fully described below.

Said distal section 36 includes a pivot area 40 which includes a substantially circular ratchet 42 which depends therefrom. The distal section as well as its constituent pivot area and ratchet are secured at an axis of rotation 44 which is defined by a rotatable connection with a proximal receiver 46 which, at proximal ends 48 thereof is secured to proximal member 25 of the orthopedic brace through the use of rivets or like means 50 and 51. Accordingly, distal section 36 is able to rotate upon axis of rotation 44 relative to proximal receiver 46 and proximal member 25 which is secured thereto.

Also secured to proximal receiver 46 is a control section 52 which includes at least three saw tooth teeth 54. As may be noted in FIG. 2, control section 52 is rotatably secured to proximal receiver 46 at an axis of rotation 56. Biasing of the control section 52 relative to the distal section 36 is accomplished through the use of an S-like spring element 58 which, as may be noted in FIG. 2, is secured at a lower end 60 to the lower surface of the control section 52 and at an upper end 62 to an upper surface of the proximal receiver 46. Therebetween posts 64 and 66 create the necessary springlike shape to assure the proper directionality and degree of biasing pressure of spring 58 against the control section 52 and, thereby of teeth 54 of the pawl 55.

Resultant of the above, it is to be appreciated that there is provided a lever 68 which may be selectably manually moved in the direction of arrow 70 to thereby selectably present engagement of the respective teeth of the above-referenced pawl 55 and ratchet 42. The teeth do not intersect a virtual line existing between the axes of rotation 44 and 56 of the distal and control sections. Thereby, movement of distal member 23 relative to proximal member 25 may be readily accomplished. After appropriate movement has been accomplished, the lever 68 is simply released and thereby permitted to lock at a new position of the pawl and ratchet.

Figure 9:
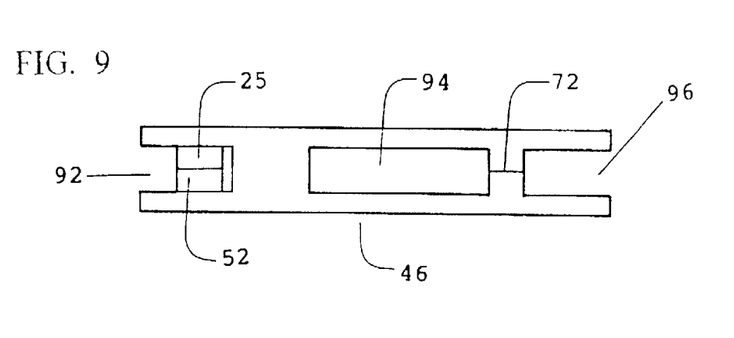
FIG. 9 is a top plan view of the proximal receiver.

Another feature of the instant invention may be seen in the view of FIG. 2 to include integral bar 72 (see also FIG. 3, 6, and 9) which acts to preclude over-rotation of the distal member 23 and associated distal section 36 relative to proximal member 25 and the associated proximal receiver 46.

In FIG. 3 is shown support points 74, 76 and 78 which reflect the manner in which distal member 23 of the brace is secured relative to the distal section 36 and its constituent elements. Also shown in the view of FIG. 3 are bending forces 80, 82 and 84 to which the hinge system of the orthopedic brace would typically be subject. It may, accordingly, be appreciated that the support points 74, 76 and 78 are strategically positioned to compensate for the bending forces 74, 76 and 78 to which the distal section are subject.

Figure 4:
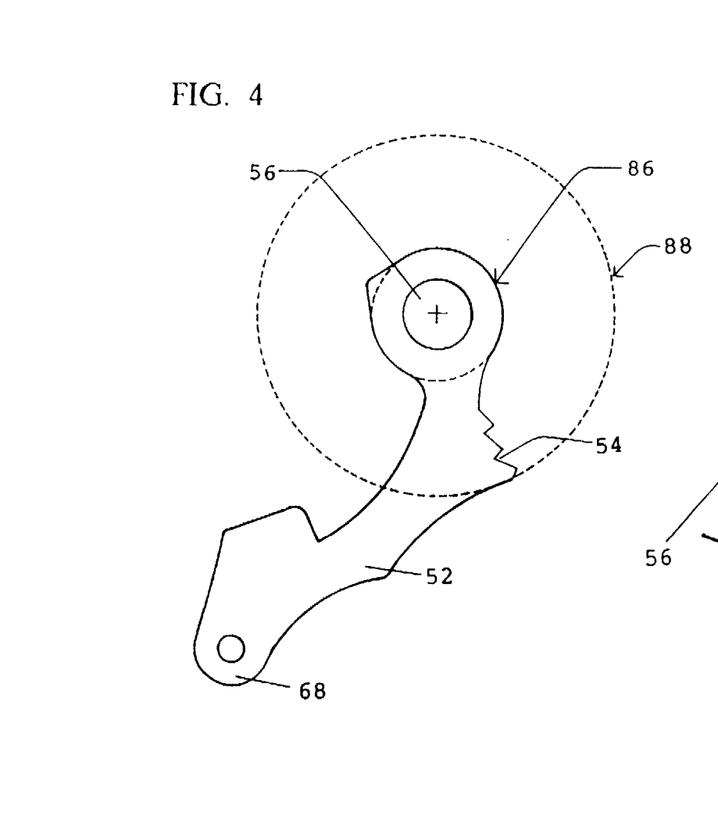
FIG. 4 is a side plan view of the pawl portion thereof.

With reference to FIG. 4, there is shown the control section 52 of the system and, more particularly, the relevant cam action lever radius 88 of the section 52 relative to that in the prior art reflected in FIG. 1. More particularly, a prior art radius 86 shows the cam leverage distance that exists in the prior art. Therein, the radius 88 shows the effective cam leverage distance in the instant invention, the consequence thereof being that the control section 52 and associated pawl may be operated with increased mechanical advantage over the prior art such that each of change of position is effected with enhanced ease and reliability in new positioning after the handle 68 of the control section 52 is released.

Figure 5:
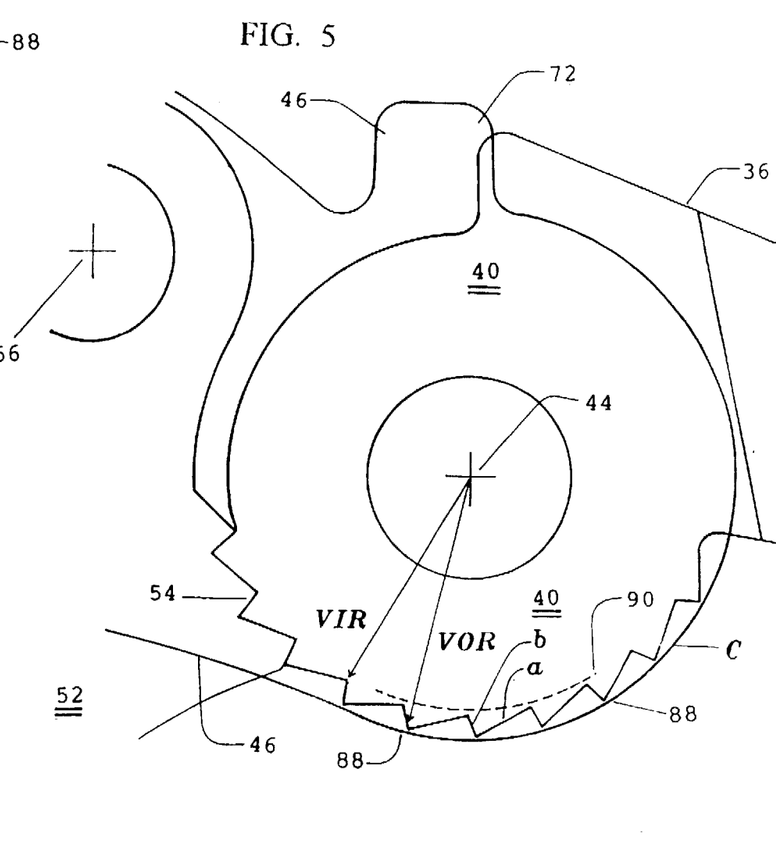
FIG. 5 is an enlarged view of the portion of FIG. 2 showing the interaction between the teeth of the pawl and ratchet including the structure of the teeth thereof.

With reference to FIG. 5, there is shown in enlarged view the teeth of the respective pawls and ratchet of the instant invention. More particularly, the ratchet 42 of the distal section 40 may be seen to be substantially circular and to include a plurality of angular saw-like teeth 86. Each of said teeth are defined by alternating major arms a and minor arms b, the intersections of which define alternating outer vertices 88 and inner vertices 90 in which each of said inner vertices 90 is tilted in a counter clockwise direction. Said inner vertices each define total included angles in a range of between about 75 and about 95 degrees, with 85 degrees preferred. Further, the ratio of the length of each major arm a to minor arm b is in a range of about 2:1 to about 3.5:1. It is further noted in FIG. 5 that said inner vertices 90 define a virtual inner radius VIR and said outer vertices 88 define a virtual outer radius (VOR) in which the ratio of the VOR to the VIR is about 1.1:1.0.

It is further noted that the major arm a of each tooth 86 within the circle C defined by the VOR intersects the tangent of C at an angle in a range of about 20 to about 40 degrees, with 30 degrees being preferable, and each minor arm b of each tooth 86 intersects the tangent of the circle C at an angle in the range of about 60 degrees to about 80 degrees, with 70 degrees being preferable. Thereby, the angle between major arm a and the VOR is about 60 degrees and between minor arm b and the VOR is about 20 degrees.

It is further noted that a 90-degree, that is, one quarter of the circle defined by the VOR within ratchet 42 will contain about 5.5 teeth so that an entire circle would contain 24 teeth, this corresponding to a subtended angle of about 15 degrees of a circle per tooth 86. In other words, the alternating major and minor arms of each tooth 86, in combination, together subtend an angle of about 15 degrees of an entire circle of the distal section 40.

It may be further noted that each tooth 86 defines a scalene triangle in which, in a preferred embodiment, the circle defined by the VOR is a virtual hypothenuse thereof. The chords of arms a and b the outer circle c defined by the VOR are in a relative ratio of about 9 to 1. In terms of ratio of length the major to minor arm, the major arm a is about three times the length of the minor arm. The gullet of each of tooth 86 is about 85 degrees but may vary between about 75 to about 95 degrees.

Figure 6:
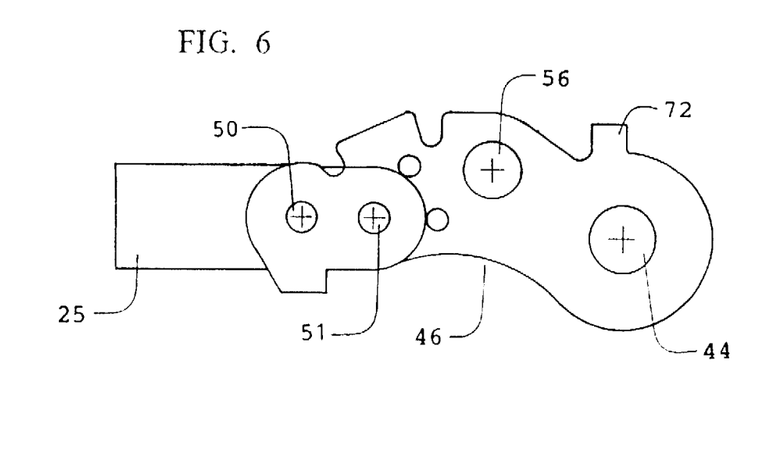
FIG. 6 is a side plan view of the proximal receiver of the present invention.
Figure 7:
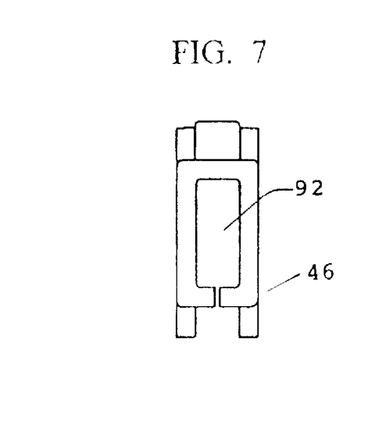
FIG. 7 is a rear plan view thereof.
Figure 8:
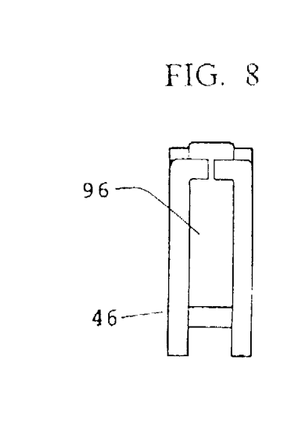
FIG. 8 is a front plan view thereof.

With reference to the views of FIGS. 6 thru 9, there is shown the proximal receiver 46 in respective, rear, front and top views. Therefrom, it may be appreciated that the transverse geometry of the proximal receiver 46 is one which provides for a four sided enclosure of proximal member 25, an advantage of which is to stabilize the proximal receiver, and the above described operational elements therewithin, against transverse and longitudinal movements relative to proximal member 25 of the brace. More particularly, in the top view of FIG. 9 may be seen openings 92, 94 and 96 which permits the placement thereinto of member 25. Within opening 94 is also placed control section 52 including pawl 55. Within opening 96 is accommodated distal section 36. In FIG. 7 is shown opening 92 into which proximal member 25 is placed and in FIG. 8 is shown opening 96 into which distal rod 23 is placed. Also shown in FIG. 6 are axes of rotation 44 and 56, as well as bar 72.

Figure 10:
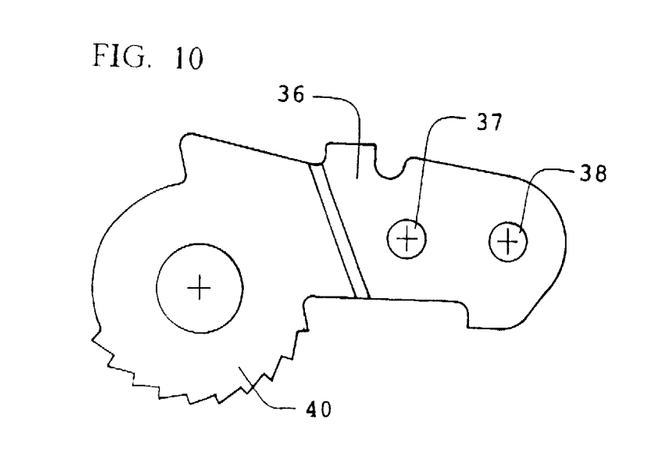
FIG. 10 is a side view of the distal section including the receiver thereof.
Figure 11:
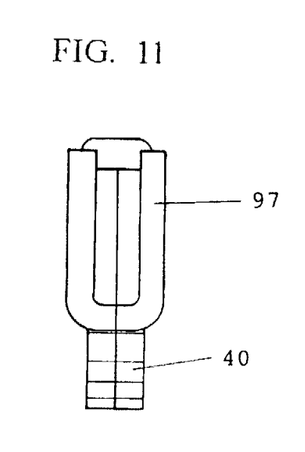
FIG. 11 is a rear end view of the receiver of the distal section of FIG. 10.
Figure 12:
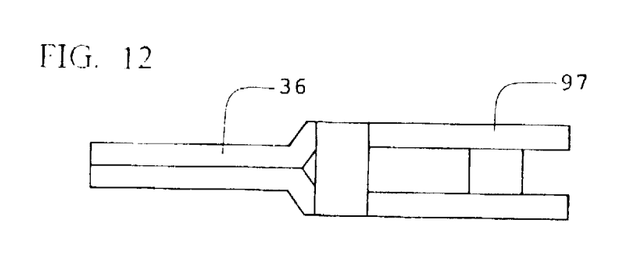
FIG. 12 is a top plan view thereof.

In the view of FIGS. 10 to 12 are is shown distal receiver portion of the distal section 36 and, thereby, the manner in which distal bar 23 may be secured into thereto at rivet points 37 and 38, above described.

Figure 13:
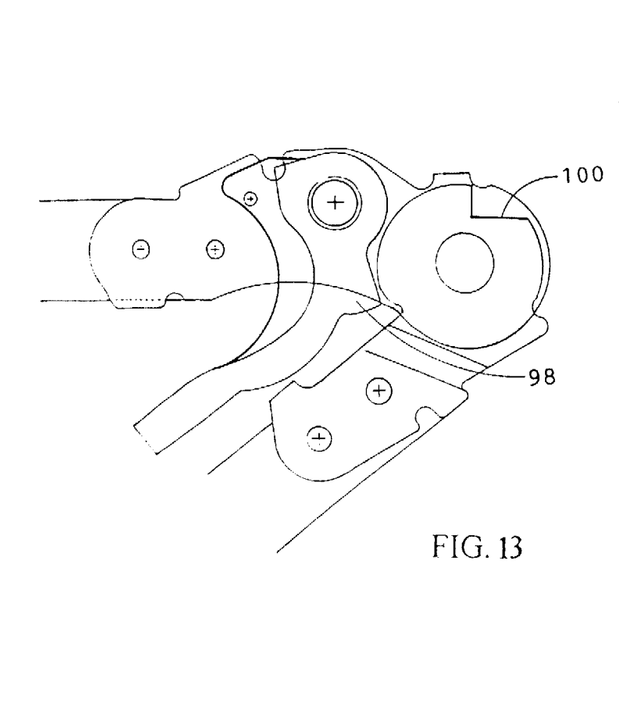
FIG. 13 is a side view of a single-toothed embodiment of the hinge system, with the brace fully retracted.
Figure 14:
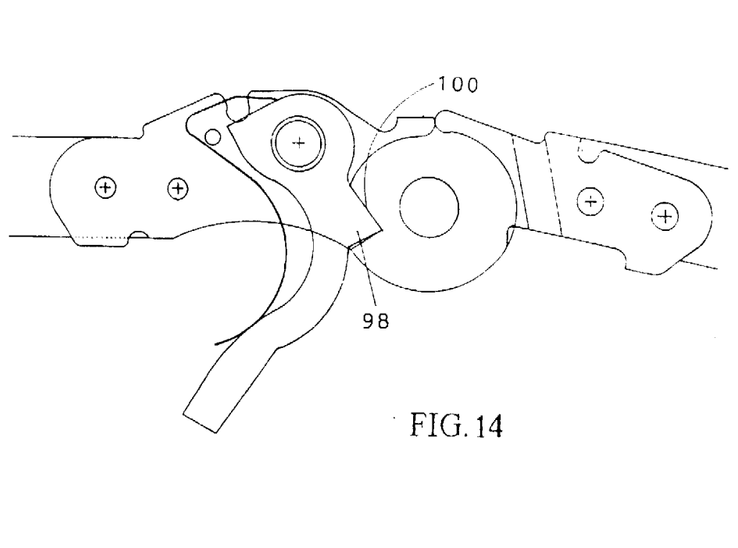
FIG. 14 is a side view of the single-toothed embodiment of the hinge system, with the brace fully extended.

As shown in FIGS. 13 and 14, the hinge system may also be embodied wherein ratchet 20 exhibits a single tooth 98 and pawl 22 uses an indentation 100 in lieu of a multiplicity of teeth. Such an embodiment is particularly suited for a patient who only requires a full retraction, as seen in FIG. 13, or full extension, as seen in FIG. 14. The single tooth 98 avails itself of the above discussed angular parameters, while the pawl 22 and its indentation 100 is complemental in geometry to the tooth 98.

Accordingly, while there has been shown the preferred embodiment of the present invention, it is to be understood that the invention may be embodied otherwise that is specifically shown and described herein, and that within said embodiment certain changes may be made in the forms and arrangements of the parts without departing from the underlying ideas or principles of this invention as set forth in the Claims appended herewith.

I claim:

1. A hinge system for an orthopedic brace, the system comprising:

(a) a distal section including a substantially circular pivot area having an axis of rotation, said area including a ratchet depending therefrom, said ratchet having a plurality of angular saw-tooth teeth, each of said teeth defined by alternating major and minor arms thereof, intersections of said arms defining alternating outer and inner vertices, each of said inner vertices tilted in a counter-clockwise direction, said inner vertices each defining total included angles of between about 75 and about 95 degrees, in which a ratio of the length of each major to minor arm is in a range of about 2:1 to about 3.5:1, said inner vertices also defining a virtual inner radius, of said ratchet, between said inner vertices and said axis of rotation of said pivot area, and each of said outer vertices defining a virtual outer radius between said vertices and said axis of rotation, in which each major arm of each tooth intersects a tangent of a circle defined by said outer radius at an angle in a range of about 20 to about 40 degrees and in which each minor arm of each tooth intersects said outer circle at an angle in a range of about 60 degrees to about 80 degrees;

(b) a control section having an axis of rotation, said section including a rotatable pawl having at least three saw-tooth teeth, each complemental in geometry to said teeth of said ratchet of said pivot area, said teeth of said pawl selectably engagable with said teeth of said ratchet, in which engagement of said teeth does not intersect a virtual line existing between said axes of rotation of said distal and control sections;

(c) release means for selectable disengagement of said teeth of said pawl from said teeth of said ratchet, to permit free rotational movement of said distal section relative to said control section of the orthopedic brace when a change in relative position therebetween is desired;

(d) a four-sided distal receiver integrally dependent from said distal section and proportioned for securable receipt of a distal member of said brace;

(e) a proximal section proportioned for securable receipt of a proximal receiver proportioned for securable receipt of a proximal member of said brace, said receiver also providing pivot axes for said pivot area of said distal section of said rotatable pawl, in which forces transmitted from and through said distal section of the brace to said ratchet are transmitted through said pawl to inner walls of said receivers, thereby exerting multi-point pressure between said pawl and said receivers, thus stabilizing the hinge system against unwanted rotation between engaged teeth and movement of said distal control sections relative to the respective distal and proximal members;

(f) biasing means for effecting said engagement of said teeth of said pawl with said teeth of said ratchet, in which said biasing means comprise a spring element mounted within the proximal section of the brace, having one end thereof selectably in contact with a rear surface of said proximal section; and (g) extension limit means integrally depending from said proximal section of said brace, said limit means defining a greatest extent of forward motion of the distal section of the brace relative to the proximal section.

2. The hinge system as recited in claim 1, further comprising:

a four sided distal receiver integrally dependent from said distal section and proportioned for securable receipt of a distal member of said brace.

3. The hinge system as recited in claim 2, further comprising:

a proximal section proportioned for securable receipt of a proximal receiver proportioned for securable receipt of a proximal member of said brace, said receiver also providing pivot axes for said pivot area of said distal section of said rotatable pawl, whereby forces transmitted from and through said distal section of the brace to said ratchet are transmitted through said pawl to inner walls of said receivers, thereby exerting multi-point pressure between said pawl and said receivers, thus stabilizing the hinge system against unwanted rotation between engaged teeth and movement of said distal control sections relative to the respective distal and proximal members.

4. The hinge means as recited in claim 3, further comprising:

extension limit means integrally depending from said proximal section of said brace, said limit means defining a greatest extent of forward motion of the distal section of the brace relative to the proximal section.

5. The hinge system as recited in claim 1, in which said release means comprises:

a lever arm secured to said axis rotation of said pawl.

6. The hinge system as recited in claim 5, in which said receivers further comprise:

machine stamped, metallic parts.

7. A hinge system for an orthopedic brace, the system comprising:

(a) a distal section including a substantially circular pivot area having an axis of rotation, said area including a ratchet depending therefrom, said ratchet having an angular saw-tooth defined by major and minor arms, the intersection of said arms defining an outer and inner vertex tilted in a counter-clockwise direction, said inner vertice defines a total included angle of between about 75 and about 95 degrees, in which a ratio of the length of the major to minor arm is in a range of about 2:1 to about 3.5:1, said inner vertice also defines a virtual inner radius of said ratchet between said inner vertice and said axis of rotation of said pivot area, and the outer vertice defines a virtual outer radius between said vertices and said axis of rotation, said major arm of the tooth intersects a tangent of a circle defined by said outer radius at an angle in a range of about 20 to about 40 degrees and in which said minor arm of said tooth intersects said outer circle at an angle in a range of about 60 degrees to about 80 degrees;

(b) a control section having an axis or rotation, said section including a rotatable pawl having an indentation complemental in geometry to said tooth of said ratchet of said pivot area, said indentation of said pawl selectably rotationally engagable with said tooth of said ratchet, in which such engagement of said tooth does not intersect a virtual line existing between said axes of rotation of said distal and control sections;

(c) release means for selectable disengagement of said indentation of said pawl from said tooth of said ratchet, to permit free rotational movement of said distal section relative to said control section of the orthopedic brace when a change in relative position therebetween is desired;

(d) a four sided distal receiver integrally dependent from said distal section and proportioned for securable receipt of a distal member of said brace;

(e) a proximal section proportioned for securable receipt of a proximal receiver proportioned for securable receipt of a proximal member of said brace, said receiver also providing pivot axes for said pivot area of said distal section of said rotatable pawl, in which forces transmitted from and through said distal section of the brace to said ratchet are transmitted through said pawl to inner walls of said receivers, thereby exerting multi-point pressure between said pawl and said receivers, thus stabilizing the hinge system against unwanted rotation between engaged teeth and movement of said distal control sections relative to the respective distal and proximal members;

(f) biasing means for effecting said rotational engagement of said indentation of said pawl into said tooth of said ratchet in which said biasing means comprise a spring element mounted within the proximal section of the brace, having one end thereof selectably in contact with a rear surface of said proximal section; and (g) extension limit means integrally depending from said proximal section of said brace, said limit means defining a greatest extent of forward motion of the distal section of the brace relative to the proximal section.

8. The hinge system as recited in claim 7, further comprising:

a four sided receiver integrally dependent from said distal section and proportioned for securable receipt of a distal member of said brace.

9. The hinge system as recited in claim 8, further comprising:

a proximal section proportioned for securable receipt of a proximal receiver proportioned for securable receipt of a proximal member of said brace, said receiver also providing pivot axes for said pivot area of said distal section of said rotatable pawl, whereby forces transmitted from and through said distal section of the brace to said ratchet are transmitted through said pawl to inner walls of said receivers, thereby exerting multi-point pressure between said pawl and said receivers, thus stabilizing the hinge system against unwanted rotation between engaged teeth and movement of said distal control sections relative to the respective distal and proximal members.

10. The hinge means as recited in claim 9, further comprising:

extension limit means integrally depending from said proximal section of said brace, said limit means defining a greatest extent of forward motion of the distal section of the brace relative to the proximal section.

11. The hinge system as recited in claim 7, in which said release means comprises:

a lever arm secured to said axis rotation of said pawl.

12. The hinge system as recited in claim 11, in which said receivers further comprise:

machine stamped, metallic parts.

* * * * *